United States Patent [19]

Cheng et al.

[11] 4,440,862
[45] Apr. 3, 1984

[54] METHOD OF DETERMINING CORROSION PROPERTIES OF ZIRCONIUM ALLOYS

[75] Inventors: Bo-Ching Cheng; Ronald B. Adamson, both of Fremont, Calif.

[73] Assignee: General Electric Company, San Jose, Calif.

[21] Appl. No.: 316,757

[22] Filed: Oct. 30, 1981

[51] Int. Cl.³ .............................................. G01N 17/00
[52] U.S. Cl. ........................................ 436/6; 73/612; 422/53; 436/908
[58] Field of Search .................... 75/177; 73/61.2; 23/230 C; 422/11, 53; 436/6, 908

[56] References Cited

U.S. PATENT DOCUMENTS

| | | | |
|---|---|---|---|
| 2,987,352 | 6/1961 | Watson | 308/241 |
| 3,097,094 | 7/1963 | Rubenstein et al. | 75/177 |
| 3,556,870 | 1/1971 | Debray et al. | 148/6.3 |
| 3,615,885 | 10/1971 | Watson | 148/6.3 |
| 4,212,686 | 7/1980 | Lunde et al. | 75/177 |

Primary Examiner—Michael S. Marcus
Attorney, Agent, or Firm—Ivor J. James, Jr.; Raymond G. Simkins; Samuel E. Turner

[57] ABSTRACT

Means for discriminating the corrosion susceptibility of alloys of zirconium in an environment of a water cooled, nuclear fission reactor.

10 Claims, 1 Drawing Figure

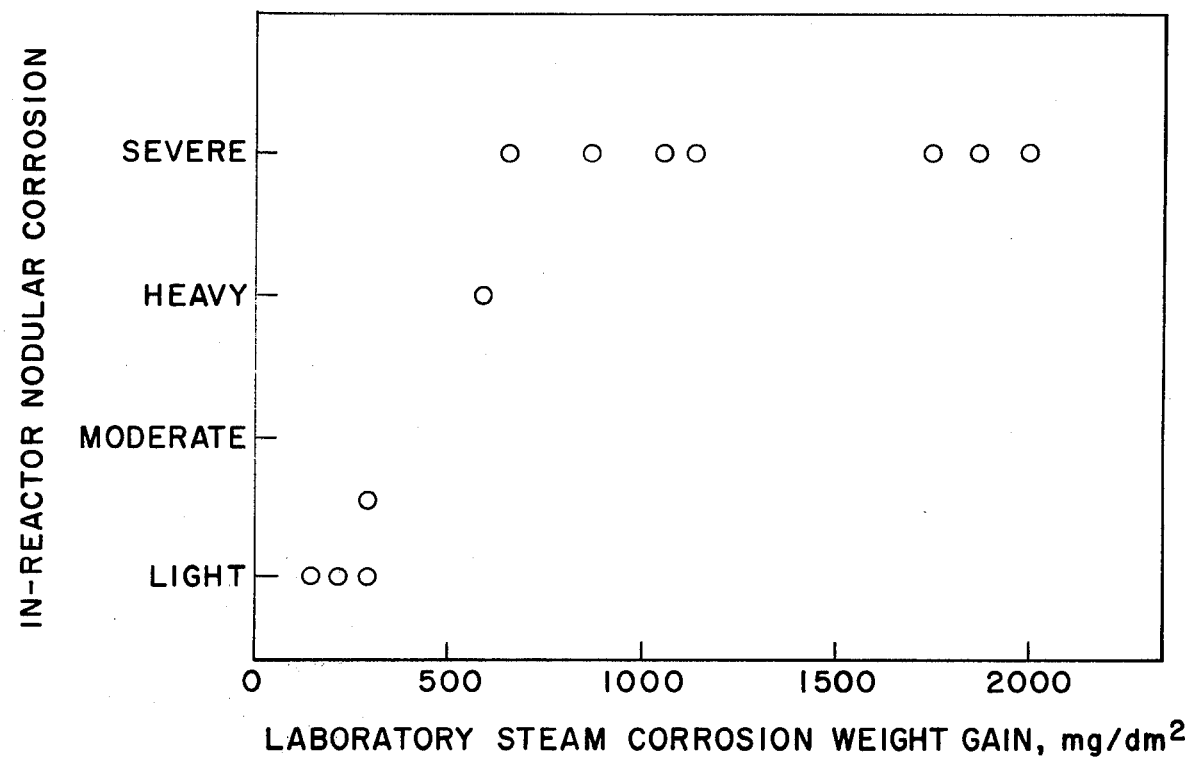

METHOD OF DETERMINING CORROSION PROPERTIES OF ZIRCONIUM ALLOYS

BACKGROUND OF THE INVENTION

Zirconium metal alloys are widely used in core components and structures of water cooled nuclear fission reactors because of their low neutron cross section, among other apt properties for such service. Note for instance U.S. Pat. No. 4,212,686. Several zirconium alloy compositions have been developed and marketed primarily for nuclear reactor applications. Typical of such alloy compositions of zirconium are the commercially available materials identified as Zircaloy-2 and Zircaloy-4, comprising alloys set forth in U.S. Pat. Nos. 2,772,964 and 3,148,055. A niobium containing alloy of zirconium for reactor service is disclosed in U.S. Pat. Nos. 3,150,972 and 4,212,686.

The Zircaloys comprise alloy compositions containing at least about 95% by weight of zirconium metal and including in percent by weight up to about 2.0% of tin, up to about 0.5% of iron, up to about 0.5% of chromium and 0 to about 0.15% of nickel.

The degree of susceptibility to corrosion of a material is a critical factor regarding its use or performance in a water cooled reactor. In a reactor environment zirconium alloys normally form a relatively innocuous, dark surface oxide uniformly and superficially thereover. This so-called black oxide provides protection to the underlying metal and thickens with increased reactor residence at a slow rate. However, zirconium alloy can further develop deleterious nodules of corrosion, sometimes referred to as pustular corrosion. The nodular type of corrosion rapidly increases in size or area and depth over the alloy surface, which under certain conditions may impair the integrity of the alloy. Nodular corrosion comprises a white oxide that can grow several times faster than the innocuous black surface oxide to produce a thick white oxide layer impeding heat transfer among the other impediments.

The degree of susceptibility to nodular corrosion of zirconium alloys when exposed to the environment of a water cooled reactor has been found to be dependent upon several or a combustion of factors, including particular alloy composition and microstructure thereof, as well as the temperatures of the reactor in operation. See, for example, the disclosures of U.S. Pat. Nos. 3,150,972, 3,261,682 and 4,212,686.

As noted in U.S. Pat. No. 4,238,251, there is an evident correlation between microstructural characteristics of a zirconium alloy composition and resistance to nodular-type of corrosion in a reactor environment.

Manipulation of the microstructure of zirconium alloys through annealing procedures has been proposed in the art as a means for improving resistance to corrosion as well as enhancing other crucial properties of such alloys for use in reactor service. U.S. Pat. Nos. 2,736,651, 2,894,866 and 3,884,728, for instance, teach reforming of the microstructure of certain alloys of zirconium to increase their structural strength and corrosion resistance in reactor service.

However, the microstructure of zirconium alloys, and in turn their corrosion susceptibility, have been found to often vary. Different or nonuniform microstructures within an alloy can result from faulty or incomplete annealing, and from metal working or fabrication operations comprising reduction or drawing, shaping or cutting procedures, and welding.

Accordingly, there can be a great deal of latitude or uncertainty as to degree of susceptibility to corrosion for reactor components such as fuel cladding and channels which are formed from a zirconium alloy composition.

The disclosure of each of the foregoing cited United States Patents is incorporated herein by reference.

SUMMARY OF THE INVENTION

This invention comprises a method of determining the relative resistance to nodular corrosion of an alloy of zirconium within the environment of a water cooled nuclear fission reactor. The discriminating method comprises subjecting a specimen of a zirconium alloy material to an atmosphere of high pressure steam applied in a sequence of increased temperatures, and then evaluating any changes that have occurred in weight or surface appearance of the specimen. The invention is capable of discriminating susceptibility of zirconium alloys to nodular-type of corrosion in terms of corrosion weight gain and also visual appearances.

OBJECTS OF THE INVENTION

It is a primary object of this invention to provide means for determining the relative resistance to corrosion for alloys of zirconium.

It is a specific object of this invention to discriminate corrosion susceptibility of zirconium alloys for their use in water cooled, nuclear fission reactor services.

BRIEF DESCRIPTION OF THE DRAWING

The drawing comprises a plotting of a correlation between corrosion occurring in a reactor with that produced by the method of this invention.

DETAILED DESCRIPTION OF THE INVENTION

In accordance with this invention corrosion susceptibility of alloys of zirconium within a reactor environment can be determined by exposing a specimen of the alloy to high pressure steam sequentially applied at two temperature levels, and thereafter evaluating any physical changes resulting therefrom.

In the performance of this invention a zirconium alloy specimen, or an appropriate sample thereof, is cleansed of all soil and foreign matter and the weight thereof accurately determined. Cleaning can be achieved by conventional means comprising an acid bath or "pickling", followed by rinsing in water.

The alloy specimen is then subjected to steam in an autoclave at a pressure within the approximate range of 1000 to 1500 pounds per square inch gauge. The temperature of the applied steam is brought up to and held at an initial level of about 300° to about 420° C. for a period of at least about 5 hours, and thereafter increased to a subsequent temperature level of about 490° to about 520° C. for a period of at least about 12 hours. Specific periods for the effective steam application comprise, after heating up to temperature, about 5 to about 15 hours at the initial temperature level of 300° to 420° C. for the initial phase, and about 12 to about 30 hours for the subsequent temperature level of 490° to 520° C.

A preferred embodiment for the practice of this invention comprises an initial steam temperature in the order to about 410° C. for a term of about 8 to 10 hours followed by a subsequent steam temperature in the order of about 510° C. for a term of about 16 to 24 hours.

Following removal from the autoclave and cooling to ambient conditions, the steam treated alloy specimen is weighed and any increase in the weight thereof is ascertained. The treated specimen can also be examined visually for an evidence of the formation of nodular corrosion on the surface thereof.

An increase in specimen weight attributable to the aforesaid process of significantly greater than about 300 to 400 milligrams per decimeter squared of surface indicates that an alloy of zirconium such as Zircaloy-2 may be susceptible to nodular corrosion. FIG. 1 illustrates this point by comparing laboratory and in-reactor corrosion performance of Zircaloy-2 tubing. The Figure shows a correlation between in-reactor nodular corrosion and results in weight gain of the laboratory stem test method of this invention carried out at 410° C. and 510° C. with Zircaloy-2 fuel rods. Also, formation of any nodular corrosion attributable to the aforesaid process covering a total surface area of the specimen of greater than about 20 to 30 percent thereof also indicates that the alloy may be susceptible to damaging nodular corrosion.

The following is a detailed illustration of the practice of a preferred embodiment of this invention.

A test sample is cut from a tubular container for nuclear fuel formed from a Zircaloy alloy composition, de-burred and cleansed. Surface oxide, if any, should be removed using an abrasive sandpaper. The cleaning comprises etching in an acid solution containing, for example, 2.5 to 5.0 volume percent of concentrated hydrofluoric acid, (HF), 45 volume percent concentrated nitric acid (HNO$_3$) and the balance distilled water.

Following etching, the sample is washed, dried and weighed to the nearest 0.2 mg.

The thus prepared sample is then suspended in an autoclave, steam applied and the system is brought to an equilibrium at 410° C. (770° F.) and pressure of about 1500 psig. This temperature-pressure equilibrium of the steam atmosphere is maintained for approximately 8 hours for the initial phase whereupon the temperature is again increased for the subsequent phase.

Upon attaining a temperature of 510° C. (950° F.), the system is again brought to equilibrium and is held at about 510° C. and about 1500 psig for approximately 16 hours for the subsequent phase.

On completion of the terms of steam treatment at both temperature levels or phases, the autoclave is brought down to ambient conditions, the test sample removed, dried and then weighed and visually examined. Any weight increase in the sample is ascertained, and the sample can be visually examined for nodular corrosion formulations.

What is claimed is:

1. A method of determining the relative resistance to nodular-type of corrosion of an alloy of zirconium in an environment of a water cooled nuclear fission reactor, comprising exposing a specimen of the alloy to high pressure steam sequentially applied at two distinct temperature levels by applying the steps of:
   (a) subjecting a specimen of an alloy of zirconium to an atmosphere of steam at a temperature of about 300° to about 420° C. at a pressure of at least about 1000 psig for a period of at least about 5 hours;
   (b) thereupon subjecting the specimen of an alloy of zirconium at an atmosphere of steam at a temperature of about 490° to about 520° C. at a pressure of at least about 1000 psig for a period of at least about 12 hours; and
   (c) ascertaining any corrosion formation on said steam exposed specimen of alloy of zirconium.

2. The method of claim 1, wherein the specimen is exposed to the steam atmosphere of step (a) for a period of about 5 to about 15 hours.

3. The method of claim 1, wherein the specimen is exposed to the steam atmosphere of step (b) for a period of about 12 to about 30 hours.

4. The method of claim 1, wherein the specimen of an alloy of zirconium is subjected to an atmosphere of steam within an autoclave under a pressure of about 1000 to about 1500 psig while at a temperature of about 300° to about 420° C. for a period of about 5 to about 10 hours, followed by a temperature of about 490° to about 520° C. for a period of about 16 to about 24 hours.

5. A method of determining the relative resistance to corrosion of an alloy of zirconium in an environment of a water cooled nuclear fission reactor, comprising subjecting a specimen of an alloy of zirconium to high pressure steam sequentially applied at two distinct temperature levels including an atmosphere of steam within an autoclave and a pressure of about 1000 to about 1500 psig for a period of about 5 to about 15 hours at a temperature of about 300° to about 420° C., and thereafter for a period of about 12 to about 30 hours at a temperature of about 490° to about 520° C., then ascertaining any weight increase in said steam exposed specimen of an alloy of zirconium.

6. The method of claim 5, wherein the specimen is subjected to steam at a temperature of about 300° to about 420° C. for a period of about 5 to about 10 hours and thereafter to steam at a temperature of about 490° to about 520° C. for a period of about 16 to about 24 hours.

7. The method of claim 5, wherein the specimen is subjected to steam at a temperature of about 400° C. for a period of about 5 to about 15 hours and thereafter to steam at a temperature of about 500° C. for a period of about 12 to about 30 hours.

8. A method of determining the relative resistance to corrosion of an alloy of zirconium in an environment of a water cooled nuclear fission reactor core, comprising subjecting a specimen of an alloy of zirconium to an atmosphere of steam within an autoclave applied sequentially at two distinct temperature levels in the following sequence of conditions:
   (a) an atmosphere of steam at a temperature of about 300° to about 420° C. at a pressure of about 1000 to about 1500 psig for a period of about 5 to about 10 hours;
   (b) thereafter an atmosphere of steam at a temperature of about 490° to about 520° C. at a pressure of about 1000 to about 1500 psig for a period of about 16 to 24 hours,
   (c) then ascertaining any weight increase in said steam exposed specimen of the alloy of zirconium.

9. The method of claim 8, wherein the specimen is exposed to an atmosphere of steam at about 400° C. for a period of about 8 to about 10 hours and thereafter to steam at about 500° C. for a period of about 16 to 24 hours.

10. The method of claim 8, wherein the specimen comprises an alloy of zironium composed of at least about 95% by weight of zirconium and including in percent by weight of up to about 0.2% of tin, up to about 0.5% of iron, up to about 0.5% of chromium and 0 to about 0.15% of nickel.

* * * * *